(12) United States Patent
Silberklang et al.

(10) Patent No.: US 8,876,377 B2
(45) Date of Patent: Nov. 4, 2014

(54) PROXIMITY DETECTION SYSTEM FOR IMAGING SYSTEMS AND METHOD FOR SENSING PROXIMITY

(75) Inventors: Alex Silberklang, Tirat Carmel (IL); Alex Fishler, Tirat Carmel (IL); Yaron Hefetz, Kibbutz Alonim (IL)

(73) Assignee: General Electric Company, Schenectady, NY (US)

( * ) Notice: Subject to any disclaimer, the term of this patent is extended or adjusted under 35 U.S.C. 154(b) by 273 days.

(21) Appl. No.: 13/336,225

(22) Filed: Dec. 23, 2011

(65) Prior Publication Data

US 2013/0163728 A1 Jun. 27, 2013

(51) Int. Cl.
| H05G 1/00 | (2006.01) |
| H01R 43/00 | (2006.01) |
| G01L 1/04 | (2006.01) |

(52) U.S. Cl.
USPC .................... 378/177; 73/862.046; 29/857

(58) Field of Classification Search
CPC ............... A61B 6/42; H05G 1/00; G01L 1/04
See application file for complete search history.

(56) References Cited

U.S. PATENT DOCUMENTS

| 4,879,508 A | 11/1989 | Andermo |
| 5,319,205 A | 6/1994 | Kline et al. |
| 5,436,700 A | 7/1995 | Kikuchi et al. |
| 5,486,700 A | 1/1996 | Silberklang et al. |
| 5,691,538 A | 11/1997 | Hitachi et al. |
| 5,828,221 A | 10/1998 | Habraken et al. |
| 6,180,943 B1 | 1/2001 | Lange |
| 6,211,523 B1 | 4/2001 | Gagnon |
| 7,531,807 B2 | 5/2009 | Hefetz |
| 7,557,352 B2 | 7/2009 | Hefetz |
| 7,723,688 B2 | 5/2010 | Hefetz |

FOREIGN PATENT DOCUMENTS

| EP | 1986084 A1 | 10/2008 |
| WO | 00/44018 A1 | 7/2000 |
| WO | 2008/063835 A2 | 5/2008 |

OTHER PUBLICATIONS

D'Ambrosio et al. (WO 2008/063835), May 29, 2008.*
Philipp (WO 00/44018). Jul. 27, 2000.*
Body Guard, Automatic Body Contouring with BrightView SPECT Series; Ray D'Ambrosio, M.S., Hugo Bertelsen MS, Jody Garrard, B.A., C.N.M.T.
Search Report and Written Opinion from PCT Application No. PCT/US2012/066174 dated Apr. 29, 2013.

* cited by examiner

*Primary Examiner* — Hoon Song
*Assistant Examiner* — Danielle Fox
(74) *Attorney, Agent, or Firm* — Dean D. Small; The Small Patent Law Group

(57) ABSTRACT

A proximity sensor array for a medical imaging system includes a flexible substrate configured to be mounted to a detector, and a plurality of sensors disposed on the substrate, the flexible substrate being deformable to contact a sensing surface of the detector. A method of fabricating a proximity sensor array and a medical imaging system are also described herein.

20 Claims, 9 Drawing Sheets

PROXIMITY DETECTION SYSTEM FOR IMAGING SYSTEMS AND METHOD FOR SENSING PROXIMITY

BACKGROUND OF THE INVENTION

The subject matter disclosed herein relates generally to imaging systems, and more particularly to proximity detection system for a medical imaging system.

Diagnostic nuclear imaging is used to study radionuclide distribution in a subject, such as a patient. Typically, one or more radiopharmaceuticals or radioisotopes are injected into the patient. Gamma camera detector heads, typically including a collimator, are placed adjacent to a surface of the patient to monitor and record emitted radiation. At least some known gamma camera detector heads are rotated around the patient to monitor the emitted radiation from a plurality of directions. The monitored radiation data from the plurality of directions is reconstructed into a three dimensional image representation of the radiopharmaceutical distribution within the patient.

Generally, the resolution of a gamma camera degrades with increasing distance between the imaged organ and the detector. In operation, it is desirable to place the gamma camera as close as possible to the patient to facilitate minimizing the loss of resolution. While it is desireable to place the gamma camera as close as possible to the patient to perform an imaging operation, it is also desireable to reposition the gamma camera to avoid contact with the patient.

Accordingly, at least some known conventional gamma cameras include a proximity sensor that alerts the operator that the gamma camera may be too close to the patient. However, conventional proximity sensors typically have a flat profile and are therefore not easily adaptable to many gamma cameras, such as for example, cameras having curved scanning surfaces. Moreover, conventional proximity sensors typical protrude a distance beyond the detector surface to enable the proximity sensor to identify a potential contact prior to the gamma cameras contacting the patient or contacting each other. The conventional proximity sensors protrude a distance to interfere or prohibit the gamma cameras from being positioned in certain scanning arrangements, such as, for example, an L-mode configuration. Moreover, the conventional proximity sensors are relatively expensive, thus increasing the overall cost of an imaging system.

BRIEF DESCRIPTION OF THE INVENTION

In one embodiment, a proximity sensor array for a medical imaging system is provided. The proximity sensor array includes a flexible substrate configured to be mounted to a detector, and a plurality of sensors disposed on the substrate, the flexible substrate being deformable to contact a sensing surface of the detector.

In another embodiment, a method of fabricating a proximity sensor array is provided. The method includes forming a plurality of sensors on a flexible substrate, the flexible substrate being deformable to contact a sensing surface of a detector, the sensors including a plurality of transmitters and a plurality of receivers arranged in rows and columns, and electrically coupling the plurality of receivers in each row in electrical series.

In a further embodiment, a medical imaging system is provided. The medical imaging system includes a gantry, at least one gamma camera coupled to the gantry, and a proximity sensor array coupled to the gamma camera. The proximity sensor array includes a flexible substrate configured to be mounted to the gamma camera, and a plurality of sensors disposed on the substrate, the flexible substrate being deformable to contact a sensing surface of the detector.

DETAILED DESCRIPTION OF THE INVENTION

Figure 1:
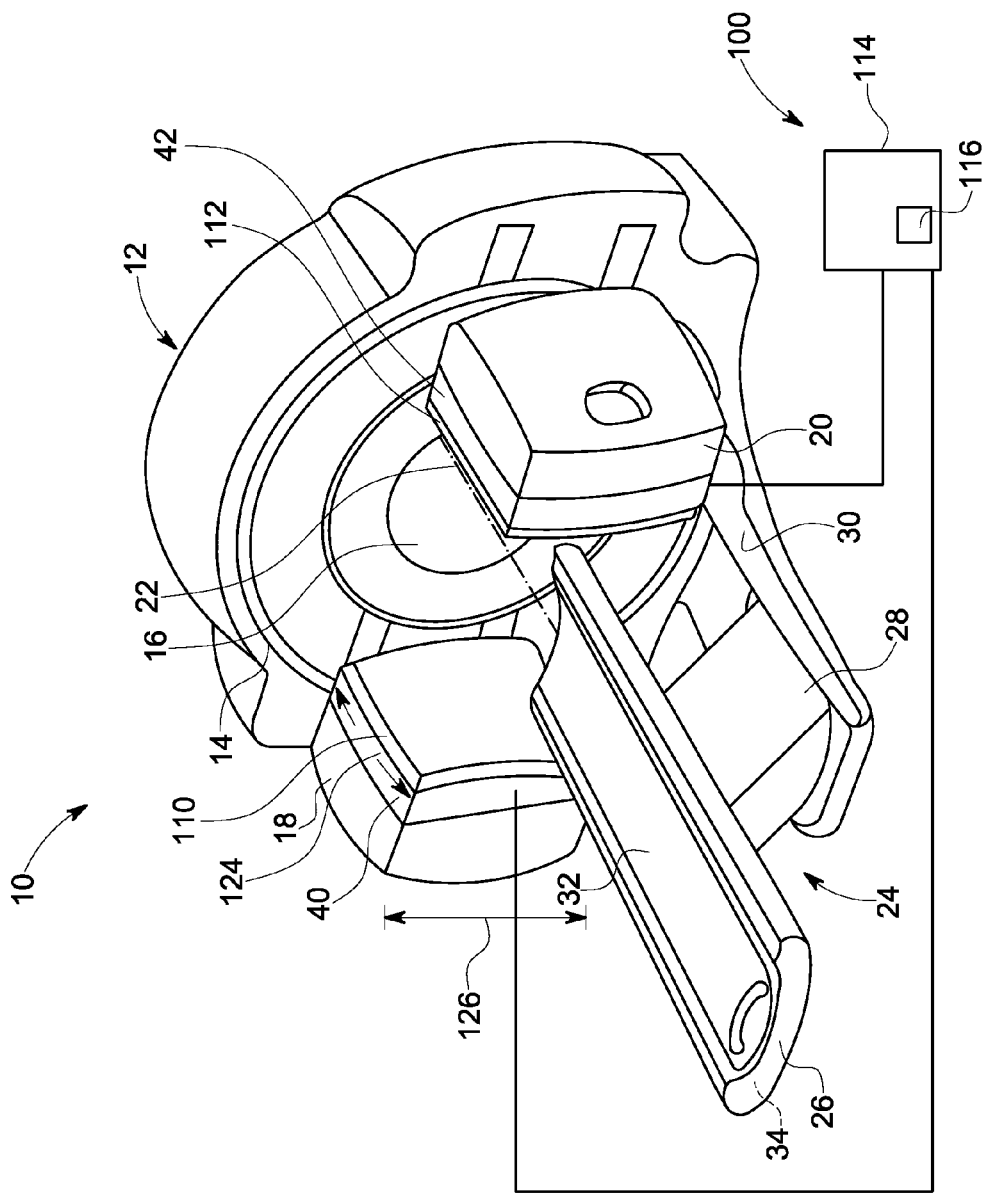
FIG. 1 is a perspective view of an exemplary imaging system constructed in accordance with various embodiments.

The foregoing summary, as well as the following detailed description of various embodiments, will be better understood when read in conjunction with the appended drawings. To the extent that the figures illustrate diagrams of the functional blocks of the various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

Described herein is a proximity detection system that may be utilized to determine the location of an object contacting one or more sensors in the detection system. More specifically, the output from the sensors may be utilized by the imaging system to either reposition at least one gamma camera or to provide a visual and/or audio indication that an object is contacting the gamma camera.

FIG. 1 is a perspective view of an exemplary nuclear medicine imaging system 10 constructed in accordance with various embodiments, which in this embodiment is a single-photon emission computed tomography (SPECT) imaging system. The system 10 includes an integrated gantry 12 that further includes a rotor 14 oriented about a gantry central bore 16. The rotor 14 is configured to support one or more nuclear medicine (NM) cameras 18 and 20. The cameras 18 and 20 may be embodied as gamma cameras, Ultra-Fast Cameras (UFC), SPECT detectors, multi-layer pixelated cameras (e.g., Compton camera), and/or positron emission tomography (PET) detectors. It should be noted that when the medical imaging system 10 is a multi-modality system, a CT camera or an x-ray camera may be provided, such as an x-ray tube (not shown) for emitting x-ray radiation towards the detectors. The rotor 14 is further configured to rotate axially about an examination axis 22.

A patient table 24 may include a bed 26 that is slidingly coupled to a bed support system 28, which may be coupled directly to a floor or may be coupled to the gantry 12 through a base 30 coupled to the gantry 12. The bed 26 may include a stretcher 32 slidingly coupled to an upper surface 34 of the bed 26. The patient table 24 is configured to facilitate ingress and egress of a patient (not shown) into an examination position that is substantially aligned with the examination axis 22. During an imaging scan, the patient table 24 may be controlled to move the bed 26 and/or stretcher 32 axially into and out of the bore 16. The operation and control of the imaging system 10 may be performed in any manner known in the art. It should be noted that the various embodiments may be implemented in connection with imaging systems that include rotating gantries or stationary gantries.

In the exemplary embodiment, the imaging system 10 also includes a proximity detection system (PDS) 100 which may form part of an automatic body contouring system (ABS) not shown. In operation, the PDS 100 facilitates maintaining the gamma cameras 18 and 20 in relatively close proximity to the imaged subject, such as for example, a patient being imaged without contacting the patient or each other. Accordingly, and in the exemplary embodiment, the PDS 100 includes a first patient safety device or sensor array 110 and a second patient safety device or sensor array 112. As used herein, an array is an arrangement of electronic parts that together form the sensor arrays 110 and/or 112. The sensor array 110 is coupled to a scanning surface of the camera 18 and the sensor array 112 is coupled to a scanning surface of the camera 20. In one embodiment, the sensor arrays 110 and 112 are coupled directly to the scanning surface of the cameras 18 and 20, respectively. In the exemplary embodiment, the cameras 18 and 20 each include a collimator, 40 and 42, respectively and the sensor arrays 110 and 112 are coupled to the scanning surface of the collimators 40 and 42.

Although the following discussion describes the construction and operation of the array sensor 110, it should be realized that the sensor array 112 is substantially similar to the sensor array 110, but disposed on a different gamma camera, for example, the gamma camera 20 shown in FIG. 1. The sensor array 110 has a length 120 and a width 122. In the exemplary embodiment, the length 120 and the width 122 are substantially the same as a length 124 and a width 126 of the scanning surface of the camera 18. In another embodiment, the length 120 and the width 122 may be selected to be smaller or larger than the length 124 and the width 126 of the gamma camera 18. For example, the length 120 and/or width 122 may be selected to be larger than either the length 124 or the width 126 of the gamma camera 18 to enable the sensor array 110 to cover a portion of the sides of the gamma camera 18 and therefore cover portions of the gamma camera 18 that may have beveled surfaces that may potentially contact surfaces of the gamma camera 20 in some modes of operation.

In the exemplary embodiment, the sensor array 110 is fabricated to be flexible to enable the sensor array 110 to be mounted flush to the surface of either the gamma camera 18 or the collimator 40 (shown in FIG. 1) when utilized. More specifically, after the sensor array 110 is coupled to the gamma camera 18, the sensor array 110 has a profile that is substantially complementary to a profile of the gamma camera 18 such that the sensor array 110 is substantially flush with, and in physical contact with, the scanning surface of the gamma camera 18. Accordingly, portions of the sensor array 110 may be fabricated using, for example, a flexible material such as, but not limited to, metal-on-polyimide, an aramid, a fluorocarbon, and a polyester.

The outputs from the sensor arrays 110 and 112 are input to a computer 114. As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer 114 is coupled to, and receives information from, the sensor arrays 110 and 112. In the exemplary embodiment, the computer 114 may include a proximity detection system module 116 that is configured to utilize the information received from the sensor arrays 110 and 112 to reposition the cameras 18 and 20 and/or to generate a visual and/or audio indication to an operator that the cameras 18 and/or 20 may contact each other or the patient. In operation, the contouring module 116 executes a set of instructions that are stored in one or more storage elements, in order to process the data received from the sensor arrays 110 and 112. The storage elements may also store data or other information as desired or needed. The storage element may be in the form of an information source or a physical memory element within either the computer 114 or the module 116.

The set of instructions may include various commands that instruct the computer or processor as a processing machine to perform specific operations such as the methods and processes of the various embodiments. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine. The set of instructions may be embodied as a tangible non-transitory computer readable medium.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

Figure 2:
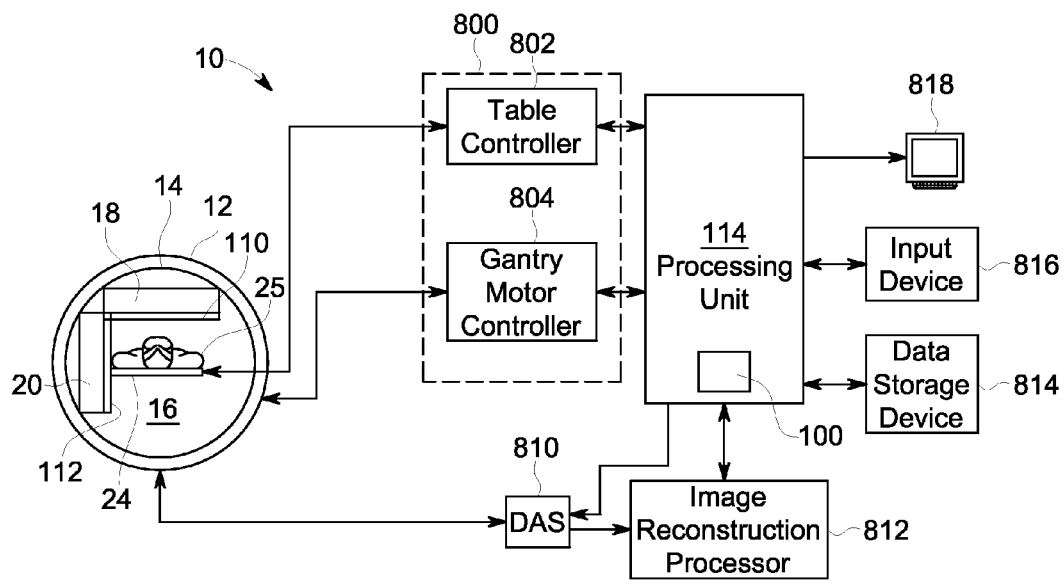
FIG. 2 is a simplified block diagram of the exemplary imaging system shown in FIG. 1.

FIG. 2 is a block diagram of the exemplary imaging system 10 shown in FIG. 1. It should be noted that the imaging system may also be a multi-modality imaging system, such as an NM/CT imaging system. The imaging system 10, illustrated as a SPECT imaging system, generally includes, as discussed above, the gantry 12 and the rotor 14 that is oriented about a gantry central bore 16. The rotor 14 is configured to support one or more NM pixelated cameras 18 and 20.

The patient table 24 is configured to facilitate ingress and egress of a patient 25 into an examination position that is substantially aligned with the examination axis 22. During an imaging scan, the patient table 24 may be controlled by a table controller unit 800 to move the patient table 24 axially into and out of the bore 16. In the exemplary embodiment, the imaging system 10 also includes the proximity detection system (PDS) 100. In operation, the PDS 100 facilitates maintaining the gamma cameras 18 and 20 in relatively close proximity to a region of interest, such as for example, a patient being imaged without contacting the patient or each other. Accordingly, and in the exemplary embodiment, the PDS 100 includes a first patient safety device or sensor array 110 and a second patient safety device or sensor array 112. The outputs from the sensor arrays 110 and 112 are input to the computer 114.

The gamma cameras 18 and 20 may be located at multiple positions (e.g., in an L-mode configuration) with respect to the patient 25. It should be noted that although the gamma cameras 18 and 20 are configured for movable operation along (or about) the gantry 12. The controller unit 80 may control the movement and positioning of the patient table 24 with respect to the gamma cameras 18 and 20 and the movement and positioning of the gamma cameras 18 and 20 with respect to the patient 25 to position the desired anatomy of the patient 25 within the fields of view (FOVs) of the gamma cameras 18 and 20, which may be performed prior to acquiring an image of the anatomy of interest. The controller unit 800 includes a table controller 802 and a gantry motor controller 804 that each may be automatically commanded by the computer 114, manually controlled by an operator, or a combination thereof. The table controller 802 may move the patient table 24 to position the patient 25 relative to the FOV of the gamma cameras 18 and 20. The imaging data may be combined and reconstructed into an image, which may comprise 2D images, a 3D volume or a 3D volume over time (4D).

A Data Acquisition System (DAS) 810 receives analog and/or digital electrical signal data produced by the gamma cameras 18 and 20 and decodes the data for subsequent processing as described in more detail herein. An image reconstruction processor 812 receives the data from the DAS 810 and reconstructs an image using any reconstruction process known in the art. A data storage device 814 may be provided to store data from the DAS 810 or reconstructed image data. An input device 816 also may be provided to receive user inputs and a display 818 may be provided to display reconstructed images.

Figure 3:
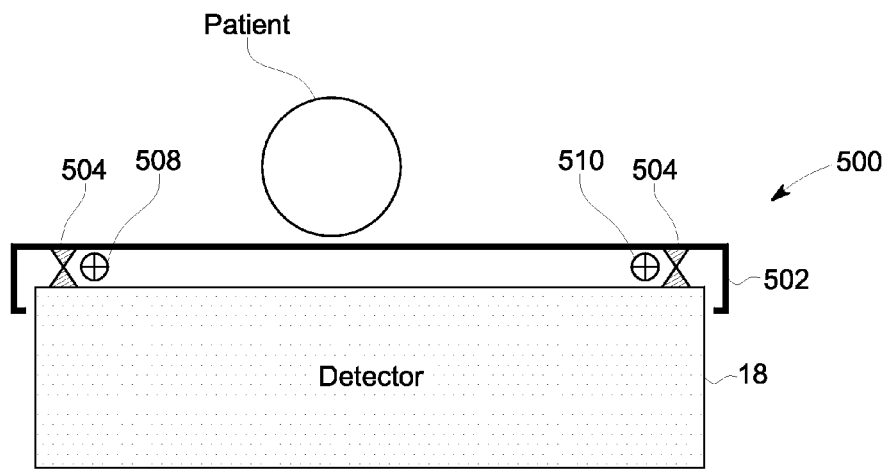
FIG. 3 is a side view of an exemplary proximity detection device formed in accordance with various embodiments.

In various embodiments, the sensor arrays described herein may also include a pressure safety device (PSD), capable of deactivating motorized motion of parts of the camera when the patient makes physical contact with the PSD thus preventing injuries to the patient. FIG. 3 schematically depicts a rigid-plate.
In various embodiments such PSD may optionally be combined or placed with a PDS according to embodiments of the invention. For example, a PSD 500 is shown in FIG. 3. The PSD 500 includes a rigid plate 502 resting on a plurality of springs 504 and having switches 510 between the plate and the detector. The PSD 500 may be integrated with a PDS by placing the capacitive PDS sensor on the plate 502. In this embodiment, the switches continue to act as in the art, providing safety. The plate 502 of PSD 500 may be made as a rigid printed circuit board (PCB). The PCB may optionally be made rigid enough to act as the plate. In the exemplary embodiment, the PSD 500 includes a substantially rigid pressure sensing plate 502, a plurality of springs 504, and micro-switches 508 and 510. For example, four micro-switches may be positioned at the corners of a substantially rectangular plate 502. In the exemplary embodiment, the sensing plate 502 is substantially rectangular and includes four springs 504, wherein a spring 504 is located at each corner of the sensing plate 502. As shown in FIG. 3, the PSD 500 may be mounted to a surface of the gamma camera 18 or optionally to a surface of the collimator 40.

In operation, when an object or the patient contacts the sensing plate 502, the sensing plate 502 is depressed. Depressing the sensing plate 502 causes the springs 504 and 506 to depress such that at least one of the micro-switches 508 and/or 510 is activated. Activating at least one of the micro-switches 508 and/or 510 causes the micro-switch to output a signal that is utilized by the imaging system to determine the location of the object contacting the PSD 500. More specifically, the output is utilized by the imaging system to halt motorized motion of camera parts that may endanger the patient. Optionally the output is utilized by the imaging system to either reposition one or both of the gamma cameras 18 and/or 20 or to provide a visual an/or audio indication that an object is contacting the gamma camera 18. It should be realized that only a single pressure sensing device is illustrated in FIG. 3, the PSD 500 may include a plurality of sensing devices that are arranged in a grid that is coupled to the surface of the gamma camera 18 or the collimator 40.

The PSD 500 may be configured to deactivate automatic control of moving parts of the imaging system 10, for example the rotor 14, the gamma cameras 18 and/or 20, and/or the bed 26, when the PSD 500 contacts a patient being scanned. After the PSD 500 detects contact with the patient or other object, in one embodiment, the system 10 stops all moving parts of system 10. Thereafter, control of the moving parts may be restricted to manual control and motion that may bring either the gamma camera 18 or the gamma camera 20 nearer to the patient being scanned, even in manual control, until contact between the PSD 500 and the patient is corrected.

Figure 4:
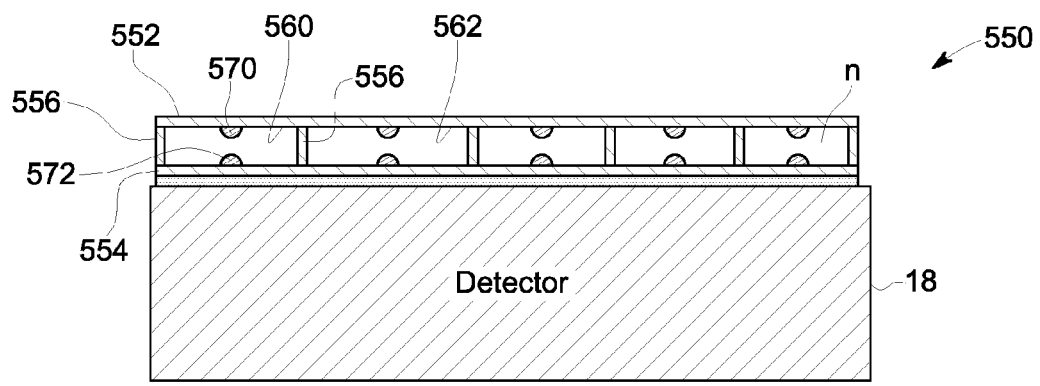
FIG. 4 is a side view of another exemplary proximity detection device formed in accordance with various embodiments.

FIG. 4 is side cross-sectional view of a portion of another exemplary PSD 550 that may be incorporated with the various sensor arrays described herein. Optionally, the PSD 550 may be utilized separately from the sensor arrays described herein. In the exemplary embodiment, the PSD 550 has a rubber structure that is glued to the detector. There is an array of contacts acting as safety switches. Moreover, a proximity sensor forming a part of the PSD 550 has a flexible upper layer with multiple contacts 552. A lower layer 554 may be rigid or flexible (however, rigid lower layer may restrict the device to a flat plane, while a completely flexible configuration allows bending the device, for example to conforms to the cylindrical shape of a nuclear camera or CT bore).

For example, in one embodiment, the PSD 550 includes an upper flexible pressure sensing plate 552, a lower pressure sensing plate 554 and a plurality of flexible dividers 556. The flexible dividers 556 are utilized to form separate sensing elements, such as for example, an element 560, and element 562 . . . n, etc. Each element, such as element 560 includes a pair of metallic pads. For example, each element includes a metallic pad 570 that is coupled to a lower surface of the sensing plate 552 and a metallic pad 572 that is coupled to an upper surface of the sensing plate 554.

In operation, when an object or the patient contacts the sensing plate 552, the sensing plate 552 is depressed. Depressing the sensing plate 552 causes the metallic pad 570 to come into physical and electrical contact with the metallic pad 572 to form an electrical circuit. In operation, the electrical circuit outputs a signal that is utilized by the imaging system 10 to determine the location of the object contacting the PSD 550. More specifically, the output is utilized by the imaging system 10 to either reposition one or both of the gamma cameras 18 and/or 20 or to provide a visual and/or audio indication that an object is contacting the gamma camera 18.

The PSD 550 may be configured to deactivate automatic control of moving parts of the imaging system 10, for example the rotor 14, the gamma cameras 18 and/or 20, and/or the bed 26, when the PSD 550 contacts a patient being scanned.

Figure 5:
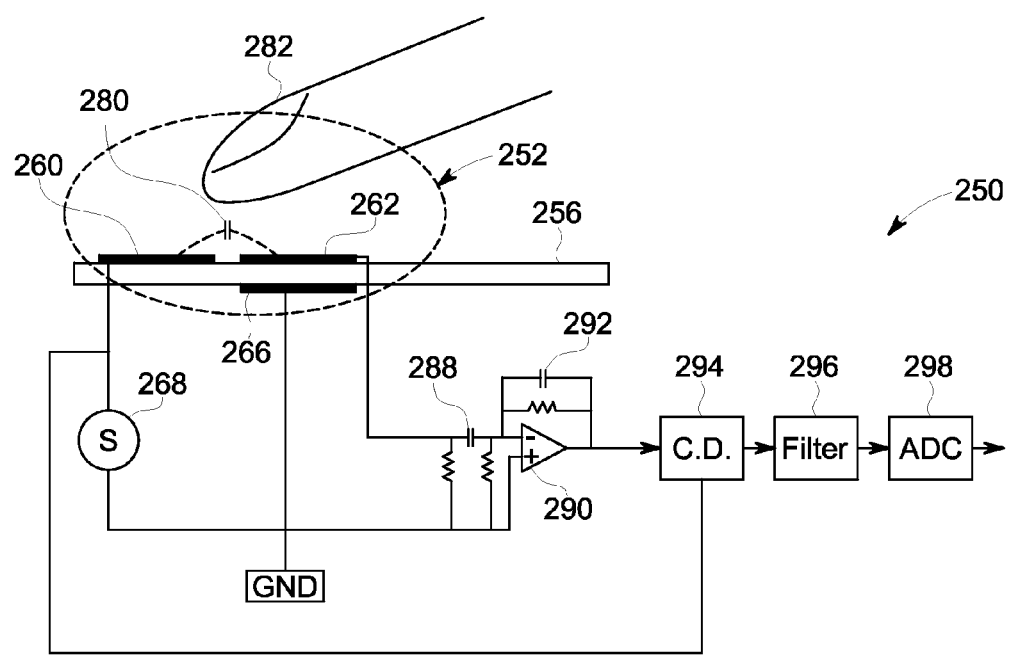
FIG. 5 is a schematic block diagram illustration of an exemplary proximity sensor cell formed in accordance with various embodiments.

FIG. 5 is a block diagram of an exemplary proximity sensor 250 formed in accordance with various embodiments. The proximity sensor 250 includes a sensor cell 252 that is connected to the electronics. The sensor cell 252 is deposited on an insulating substrate 256. The proximity sensor 250 includes a transmitter electrode 260, a receiver electrode 262, and optionally a ground electrode 266 that optionally has similar dimensions to the receiver electrode 262 and is disposed on an opposite side of the substrate 256 from the receiver electrode 262. The proximity sensor 250 also includes a signal source 268 that in one exemplary embodiment, is a 600 kHz, 10V sinusoidal signal source that is connected to the transmitter electrode 260. In operation, there is a small equivalent capacitance 280 between the transmitter electrode 260 and the receiver electrode 262. In operation, when a conductive and potentially grounded object, such as a finger 282 or other patient body part is near the sensor cell 252 it interferes with the current flow from the transmitter 260 to the receiver 262, causing a change in that current. A possible explanation is that the electromagnetic field is disturbed and the coupling between the transmitter 260 and receiver 262 is decreased, thus the signal detected will decrease. The sensor 250 may include an optional capacitor 288 that is an AC coupler of a current follower amplifier 290 (having a feedback capacitor 292 in the loop). In operation, an AC/DC converter 294 is a synchronized rectifier (preferred for small signal rectification and noise rejection; however other rectification means such as Diode Bridge, a "Precision rectifier" or a "lock in amp" rectifier may be utilized. The rectified signal is optionally "low pass filtered" by an optional filter 296 to remove noise and ripple, and digitized by an analog/digital converter 298, analyzed 116 and transmitted to the motion controller 804 shown in FIG. 2.

For example, during SPECT data acquisition the information may be used by the motion controller 804 to move the detectors such that the distance between them and an object 282 is maintain as small but safe distance in spite of the gantry rotation and possible patient motion such as breathing.

Figure 6:
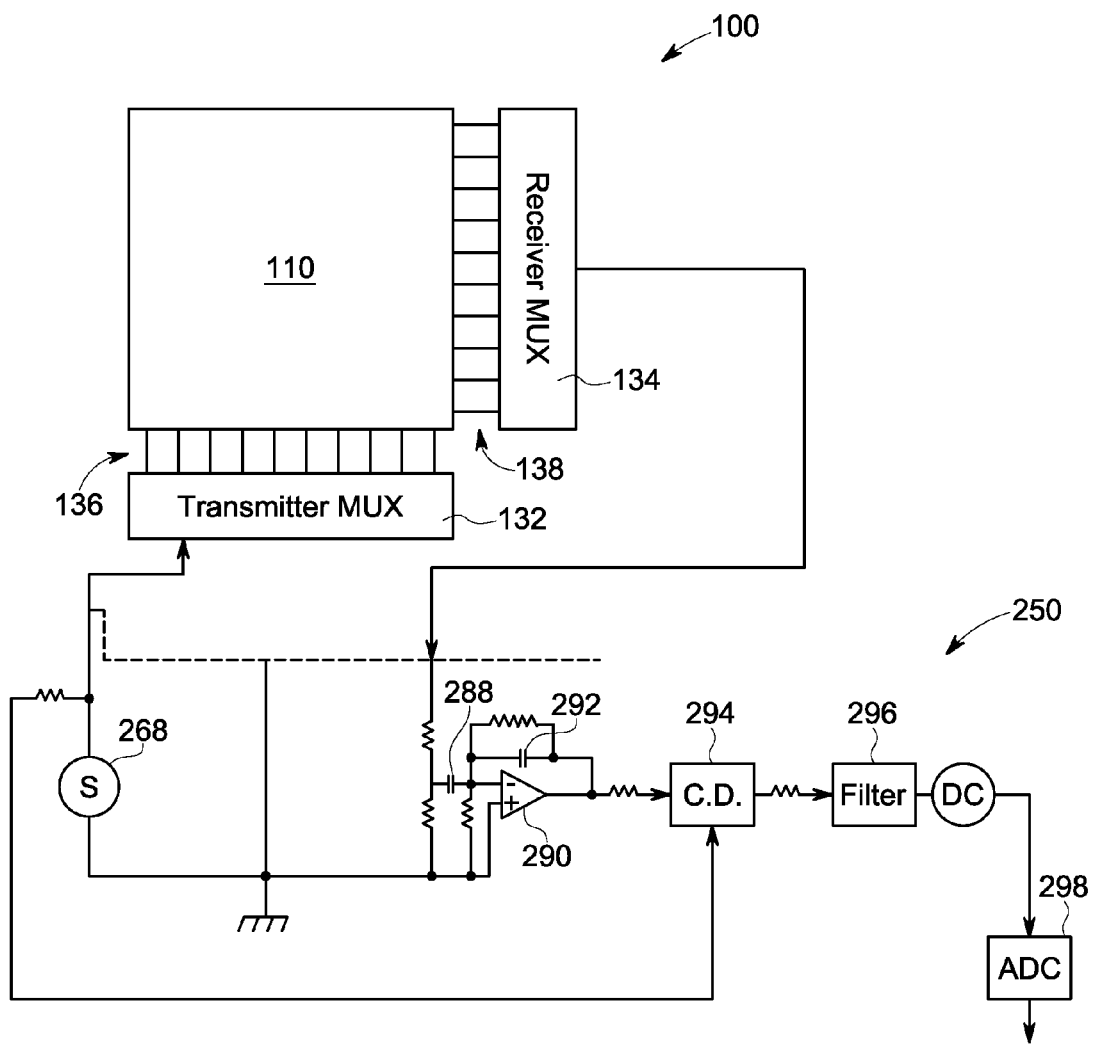
FIG. 6 is a simplified schematic illustration of the exemplary proximity detection system shown in FIGS. 4 and 5 in accordance with various embodiments.

FIG. 6 illustrates the proximity sensor 250 shown in FIG. 5 coupled to an exemplary sensor array 110. More specifically, FIG. 6 shows the muxing of transmitter and receiver channels. It should be realized that the motion of the detectors is slow, thus, the distance to the patient is generally sampled up to few times a second. Frequent sampling, allows for reduction in the complexity, cost and energy consumption of the system by serially sampling locations (sensor cells) on the surface of the proximity sensor (PDS), one at a time. In various embodiments, muxing is optional, and there are many possible muxing strategies. To be sensitive to a small body part such as a finger or the tip of the nose, a "transmitter/receiver pair" should be of an area similar to the body part: for example ~1×1 1×2 or 2×2 cm (but other sizes may be used), thus, on a 60×50 cm detectors there are ~750 to 3000 such transmitter/receiver pairs. In various embodiments, each transmitter/receiver pair may be wired individually. However, the muxing allows interrogating one (or more) pairs at a time. Moreover, different frequencies may be utilized for each active transmitters, and use coherent detection.

In the exemplary embodiment, the system 100 includes at least the sensor array 110, a transmitter multiplexer 130, and a receiver multiplexer 132. In the exemplary embodiment, the sensor array 110 includes a plurality of sensing elements that are discussed in more detail below. In operation, the transmitter multiplexer 132 transmits a signal to various sensing elements on the sensor array 110 via a plurality of input lines 136. Moreover, the receiver multiplexer 134 receives a plurality of output signals from the sensor array 110 via a plurality of output lines 138. In the exemplary embodiment, the transmitter multiplexer 1320 and the receiver multiplexer 134 may be mounted on a side of the gamma camera 18. Optionally, the transmitter multiplexer 132 and the receiver multiplexer 134 may be located remote from the gamma camera 18, within, for example, the computer 114 or incorporated within the proximity detection system module 116. In operation, the inputs supplied to the sensor array 110 via the transmitter multiplexer 132 and the outputs received from the receiver multiplexer 134 may be utilized to either reposition the gamma camera 18 or to provide a visual and/or audio indication that the gamma camera is close to and/or contacting either the gamma camera 20, the patient being imaged, or any other object detected by the sensor array 110.

Figure 7:
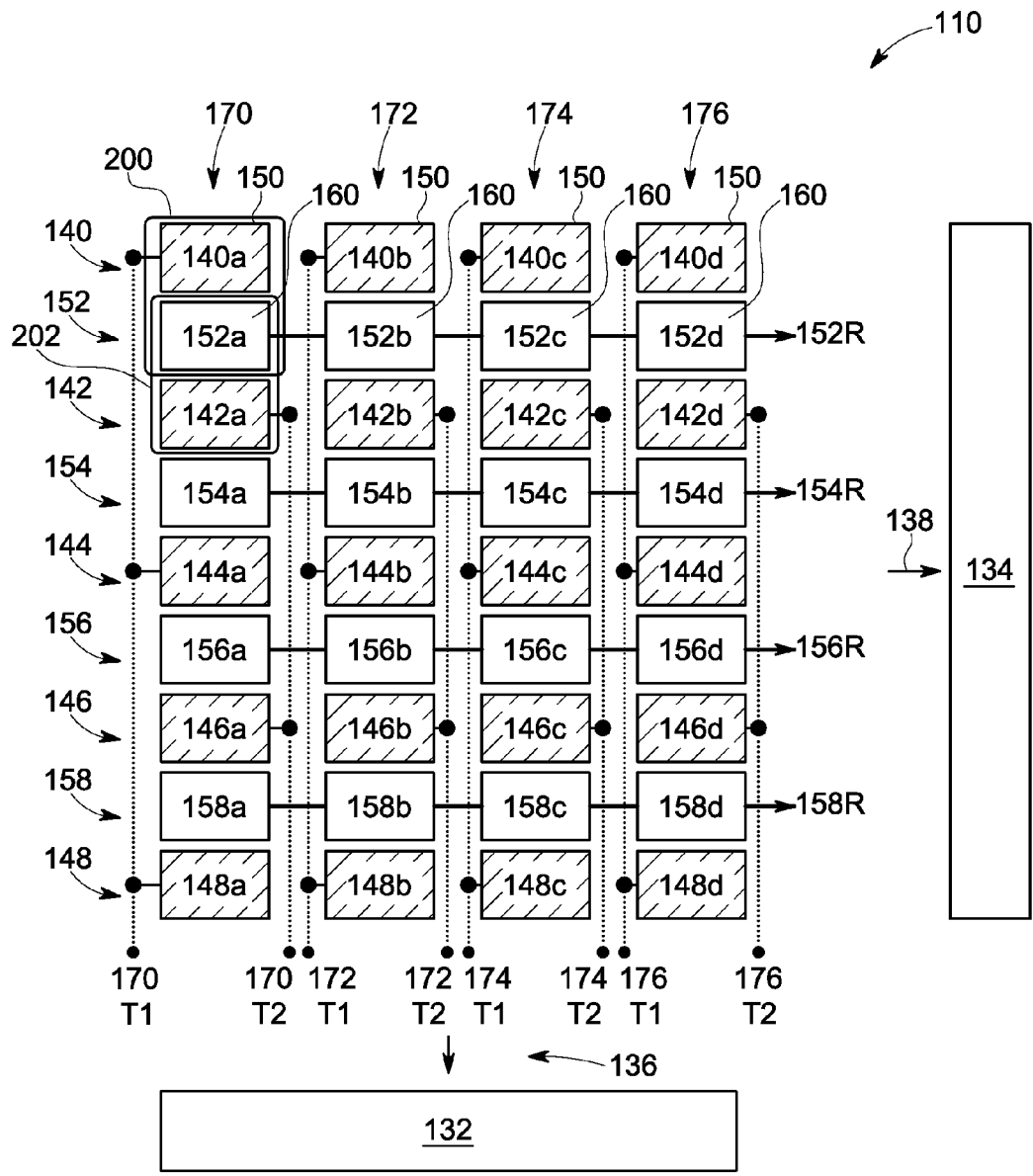
FIG. 7 is a simplified block diagram of a portion of the proximity detection system (PDS) shown in FIG. 7 in accordance with various embodiments.

The sensor array 110 includes a plurality of transmitters and receivers that are arranged in rows and columns. For example, referring to FIG. 7, the sensor array 110 is shown as including five rows 140, 142, 144, 146, and 148 of transmitters 150 and four rows 152, 154, 156, and 158 of receivers 160. It should be realized that although FIG. 7 illustrates only nine rows of transmitters and receivers, that in the exemplary embodiment, the sensor array 110 includes more than nine rows of transmitters and receivers.

The sensor array 110, in one embodiment, is configured such that rows of transmitters are interleaved with rows of receivers. For example, the row 142 of transmitters 160 is disposed between a pair of rows 152 and 154 of receivers 160. Accordingly, in the exemplary embodiment, each respective row of transmitters is positioned adjacent to at least one row of receivers such that no two rows of transmitters or receivers are disposed adjacent to each other. Moreover, the transmitters 150 and the receivers 160 are also arranged in columns, such as, for example, columns 170, 172, 174, and 176. As shown in FIG. 7, each respective column 170, 172, 174, and 176 is arranged such that the transmitters 150 are interleaved with the receivers 160. For example, the transmitter 142a is disposed between a pair of receivers 152a and 154a. Accordingly, in the exemplary embodiment, each respective transmitter 150 is positioned adjacent to at least two receivers 160 such that no two transmitters or receivers are disposed adjacent to each other.

The receivers in each respective row of receivers are coupled together electrically. For example, the receivers 152a, 152b, 152c, and 152d in row 152 are coupled together; receivers 154a, 154b, 154c, and 154d in row 154 are coupled together; receivers 156a, 156b, 156c, and 156d in row 156 are coupled together; and receivers 158a, 158b, 158c, and 158d in row 158 are coupled together. Moreover, the outputs from each of the respective receivers in a single row are transmitted to the receiver multiplexer 134 via a single output line.

For example, in operation when an output is requested from the row 152, the outputs from each of the receivers 152a, 152b, 152c, and 152d in the row 152 are transmitted concurrently to the receiver multiplexer 134 via an output line 152R. Additionally, the outputs from the receivers 154a, 154b, 154c, and 154d in row 154 are transmitted concurrently to the receiver multiplexer 134 via an output line 154R. The outputs from receivers 156a, 156b, 156c, and 156d in row 156 are transmitted concurrently to the receiver multiplexer 134 via an output line 156R, and the outputs from receivers 158a, 158b, 158c, and 158d in row 158 are transmitted concurrently to the receiver multiplexer 134 via an output line 158R.

As shown in FIG. 7, and in the exemplary embodiment, various transmitters are coupled together such that at least a portion of the transmitters, in each respective column, are coupled together electrically. More specifically, transmitters for each respective column are coupled together such that alternating transmitters, or every other transmitter, is coupled to the same input line.

For example, the transmitters 140a, 144a, and 148a in column 170 are coupled together; the transmitters 142a and 146a in column 170 are also coupled together. Moreover, the transmitters 140b, 144b, and 148b in column 172 are coupled together and the transmitters 142b and 146b in column 172 are also coupled together, the transmitters 140c, 144c, and 148c in column 174 are coupled together; the transmitters 142c and 146c in column 174 are coupled together, the transmitters 140d, 144d, and 148d in column 176 are coupled together; and the transmitters 142d and 146d in column 176 are also coupled together.

Accordingly, in operation when an input signal is input to the sensor array 110, via an input line 170T1, the input signal is subsequently supplied to the transmitters 140a, 144a, and 148a in column 170 because transmitters 140a, 144a, and 148a are coupled together in series. Additionally, when an input signal is supplied to the sensor array 110, via an input line 170T2, the input signal is subsequently supplied to the transmitters 142a and 146a, an input signal supplied to the sensor array 110, via an input line 172T1 provides an input to the transmitters 140b, 144b, and 148b in column 172, an input signal supplied to the sensor array 110, via an input line 172T2 provides an input to the transmitters 142b and 146b in column 172, an input signal supplied to the sensor array 110, via an input line 174T1 provides an input to the transmitters 140c, 144c, and 148c in column 174, an input signal supplied to the sensor array 110, via an input line 174T2 provides an input to the transmitters 142c and 146c in column 174, an input signal supplied to the sensor array 110, via an input line 176T1 provides an input to the transmitters 140d, 144d, and 148d in column 176, and an input signal supplied to the sensor array 110, via an input line 176T2 provides an input to 142d and 146d in column 176. It should be realized that although the output lines 136 (seen in FIG. 6) are shown as being on a first side of the sensor array 110 and the input lines 138 (seen in FIG. 6) are shown on a different side of the sensor array, the output and input lines may be disposed on any side of the sensor array 100 or on the same side of the sensor array 110.

In operation, the input and output lines 136 and 138 are activated/and or deactivated in a predetermined sequence to both supply input signals to the sensor array 110 and to also receive information from the sensor array 110. An adjacent transmitter and receiver may form a sensing cell. A cell, as used, in various embodiments defines a single transmitter and a single transceiver on the sensor array 110. Accordingly, the sensor array 110 includes a plurality of cells. For example, as shown in FIG. 7, the sensor array includes a cell that may be defined by the transmitter 140a and the receiver 152a. A cell may include the transmitter 142a and the receiver 154a, etc. As can be seen in FIG. 7, a cell includes a single transmitter and a single receiver in the same column. Moreover, a cell may include a transmitter and an adjacent receiver whether the receiver is above or below the transmitter in the same column. For example, a cell may include the transmitter 148d and the receiver 158d.

In operation, the sensor array 110 is iteratively scanned to determine if contact with any portion of the sensor array 110 has occurred. Initially an input signal is supplied via the input line 170T1, to transmitters 140a, 144a, and 146a. Accordingly, if the cell 200 detects an object, via a capacitance that occurs between a transmitter and a receiver, the signal from the input line 170T1 will be transmitted to the output line 152R via the combination of the transmitter 140a and the receiver 152a. More specifically, although the input signal is supplied to 140a, 144a, and 146a, only the receiver 152a, which in combination with the transmitter 140a forms the cell 200 is read via the output line 152R. Thus, only a single cell is read at a time to determine if an object has come close to, and influenced the cell. Next, for example, the cell 202, which includes the transmitter 142a and the receiver 154a may be read. To read the cell 202, an input signal is supplied via the input line 170T2, to transmitters 142a and 146a. Accordingly, if the cell 202 detects an object, the signal from the input line 172T2 will be transmitted to the output line 152R via the combination of the transmitter 142a and the receiver 154a. More specifically, although the input signal is supplied to transmitters 142a and 146a, only the receiver 154a, which in combination with the transmitter 142a which forms the cell 204, is read via the output line 154R. Thus, only a single cell is read at a time to determine if an object has come close to, and influenced the cell. It should be realized that the transmitters 150 and the receivers 160 may be arranged to form a wide variety of arrays and cells. Moreover, it should be realized that in the exemplary embodiment, only one cell is read at a time, via the operation of the input and output lines. In this arrangement a location of an object in close proximity to, or actually contacting a portion of the sensor array 110, may be specifically identified by determining the exact cell indicating that a contact or touch has occurred. Reading one cell (or few cells, depending on MUXing strategy) at a time improves the Signal to Noise Ratio (SNR) and improves reliability and sensitivity of proximity detection.

More specifically, when transmitter line 170T1 is activated, the transmitter electrodes 140a, 144a, and 149a are powered. If, at that time line 152R is activated, currents from receiver electrodes 152a, 152b, 152c and 152d are summed and detected. Thus, only "sensor cell 200" is effectively detecting presence of patient above it. On the other hand, if the transmitter line 170T2 is activated, then transmitter electrodes 146a, and 142a are powered. If at that time line 152R is activated, currents from receiver electrodes 152a, 152b, 152c and 152d are summed and detected. Thus, only "sensor cell 202" is effectively detecting presence of patient above it. In the exemplary embodiment, the configuration shown in FIG. 7 may be implemented using a plurality of layers that include for example, two conductive layers, one on each side of the PCB, or a one-sided, two-layer PCB or a three layers PCB, or other known PCB manufacturing techniques. Not seen in this figure are the optional ground pads 266' that are positioned, each under (opposite to the direction towards the patient) a corresponding receiver pad. These will be seen in several cross sectional views and in FIG. 8a-8c.

Figure 8A:
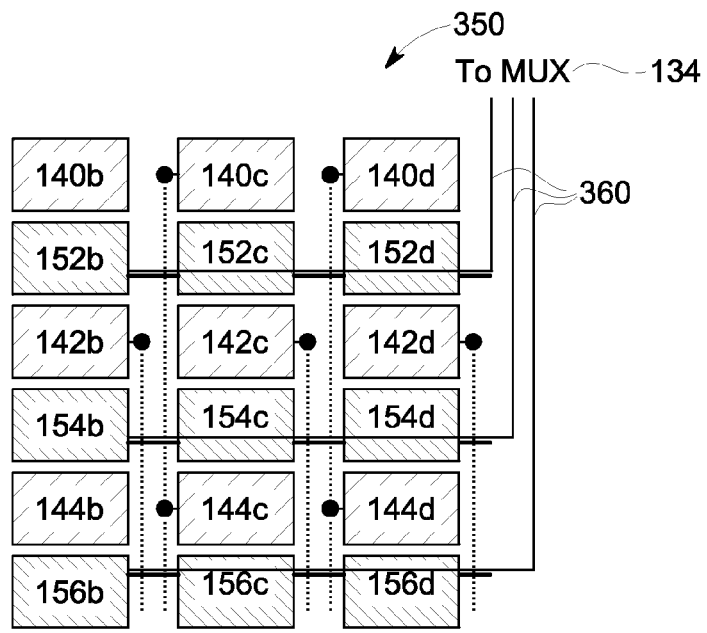
FIGS. 8A, 8B, and 8C are simplified PCB conductive layers' layouts of a portion of the proximity detection system shown in FIG. 7.
Figure 8B:
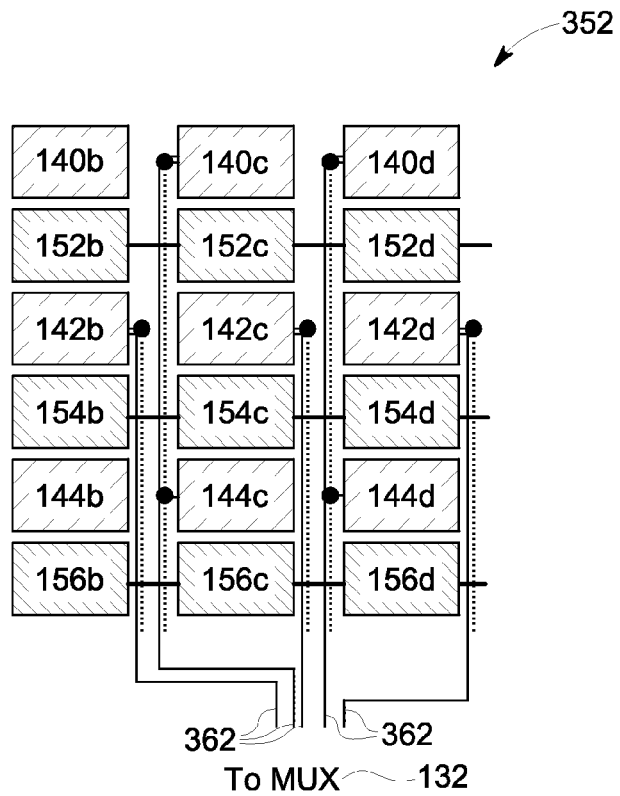
Figure 8C:
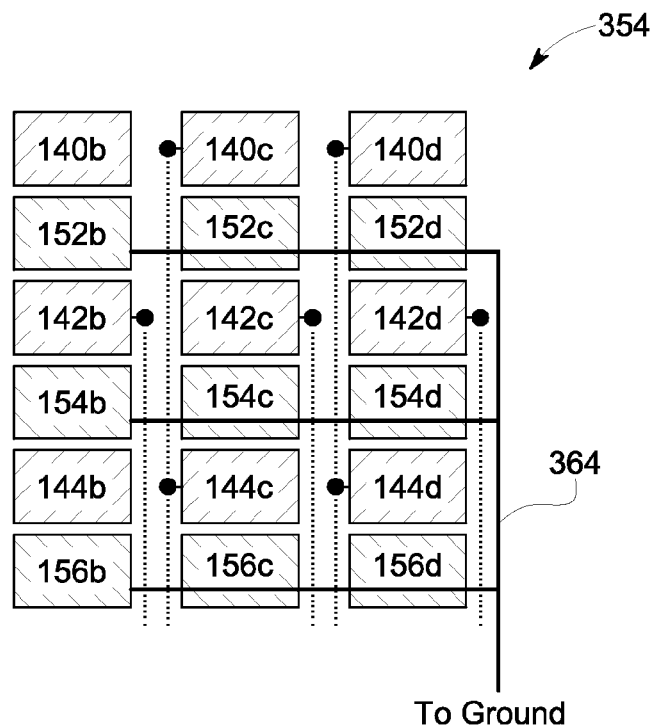

FIGS. 8A, 8B, and 8C, respectively show different conductor layers in a three layers PCB that may be utilized to form the sensor array shown in FIG. 7. In the exemplary embodiment, FIG. 8A illustrates an exemplary top layer 350 that may be formed to include the receiver electrodes and connecting lines 360 to the receiver MUX 134. FIG. 8B is a central layer 352 that may be formed to include the transmitter electrodes and connecting lines 362 to the transmitter MUX 132. FIG. 8C is an optional bottom layer 354 that shows the ground electrodes 266' and connecting line 364 grounding the ground electrodes. In an exemplary embodiment, layers 350 and 352 may be deposited on the side of the substrate that is close to the patient, while layer 354 may be deposited on the opposite side of the substrate (as seen in the example of FIG. 5. The optional ground electrodes serve to reduce coupling of signals from transmitters to receivers which is not via the effective capacitance formed by the detected object (for example by isolating the receivers from signals being coupled to the conductive structures of the gamma camera such as the collimator), thus improving the SNR. It should be realized that FIGS. 8A-8C are exemplary, and that the sensor arrays described herein may be fabricated in other manners. For example, the transmitters and the ground electrodes may be formed on the same layer, and the connecting traces routed using "vias".

Figure 9:
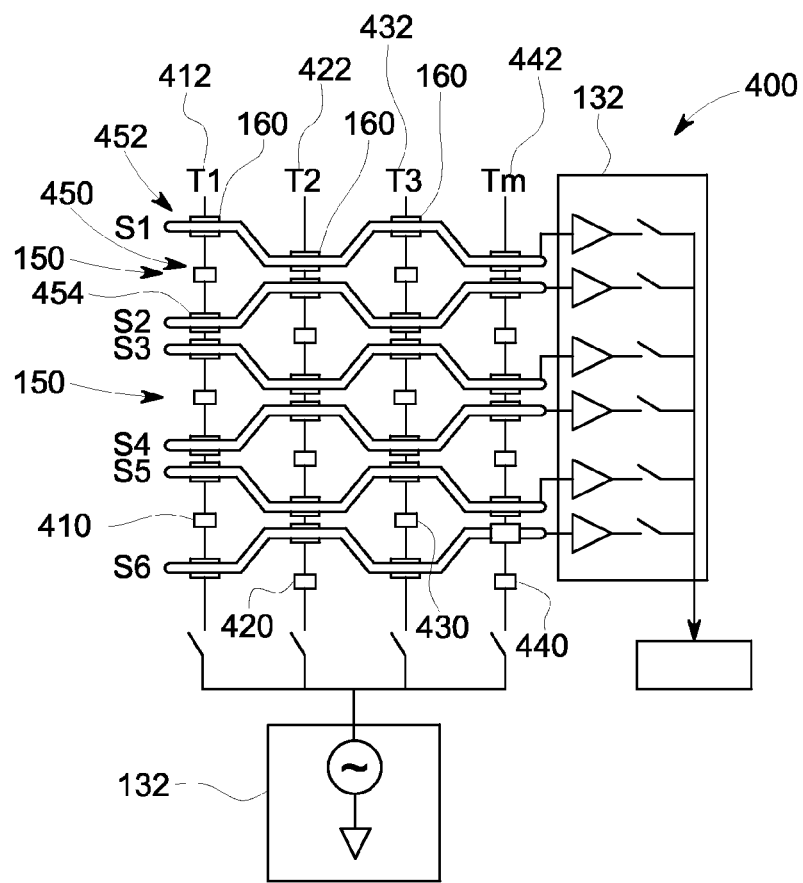
FIG. 9 is a simplified schematic illustration of another exemplary proximity detection sensor array that may be utilized with the imaging system shown in FIG. 1 in accordance with various embodiments.

FIG. 9 is a plan view of another exemplary sensor array 400. The sensor array 400 also includes a plurality of transmitters 150 and receivers 160 that are configured to perform differential sensing. In this embodiment, the transmitters 160 and the receivers are arranged in columns. Moreover, each transmitter 150 is disposed between a pair of receivers 160. Additionally, both the transmitters 150 and receivers 160 are staggered from column to column such that a transmitter 410 in a first column 412 is offset from a transmitter 420 in a second column 422. Moreover, a transmitter 430 in a third column 432 is offset from a transmitter 440 in a fourth column 442. Additionally, the transmitter 410 is disposed parallel to the transmitter 430 and the transmitter 420 is disposed parallel to the transmitter 440.

In this embodiment, the transmitters in each column are coupled together and the receivers in each row are coupled together. Accordingly, in operation and similar to sensor array 110 described above, each row of receivers is read sequentially. More specifically, an input signal is first supplied to the column 412 of transmitters. Next, a single row of receivers is read, for example, row S1. As discussed above, even though a signal is supplied to each transmitter in the column 412, only a single row of receivers is read. Therefore, a cell that includes, for example, a transmitter 450 and a receiver 452 is defined and read separately from the other cells, such as a cell that includes the transmitter 450 and a receiver 454.

Figure 10:
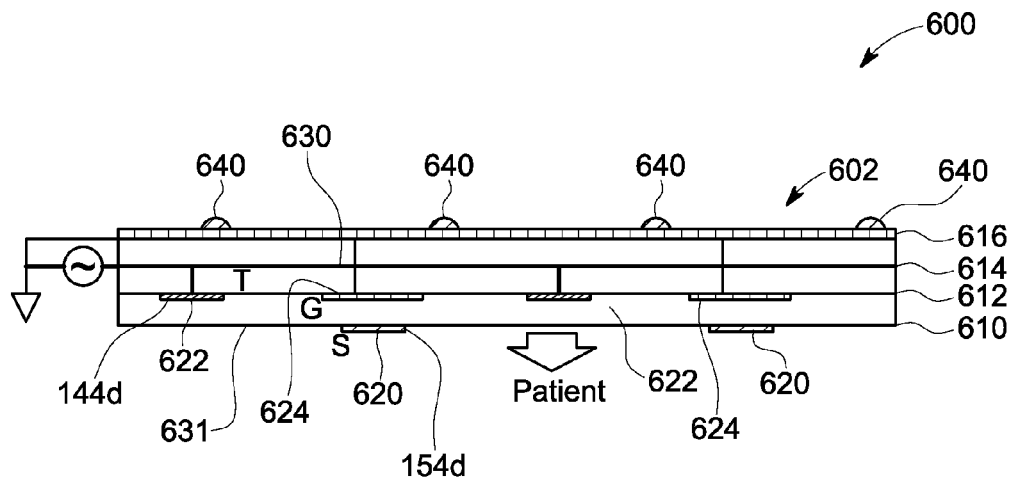
FIG. 10 is a side cross sectional view of further exemplary proximity detection system (PDS) combined with a pressure safety device (PSD) formed in accordance with various embodiments.

FIG. 10 is side cross sectional view of a portion of another exemplary sensor array 600 that includes a proximity sensor system 602 that may be incorporated with the sensor array 600 or various other sensor arrays described herein. Specifically, FIG. 10 illustrates a proximity sensor and a flexible PSD formed in one device. In the exemplary embodiment, the sensor array 600 includes four PCB layers 610, 612, 614, and 616. In this embodiment, a plurality of receivers 620 are disposed on the layer 610 and a plurality of transmitters 622 are disposed on the layer 612. The sensor array 600 also includes a plurality of ground electrodes 624, wherein each respective ground is disposed proximate to a respective receiver 620. The sensor array 600 further includes a plurality of electrical connection lines 630 disposed for example on the third layer 614 that electrically couple each respective transmitter 622 to the transmitter multiplexer 132 described above.

The sensor array 600 further includes a plurality of electrical connection lines 631 disposed for example on the first layer 610 that electrically couple each respective receiver 620 to the receiver multiplexer 134 described above. The fourth layer 616 is formed as ground plane to include a plurality of metallic pads 640.

In operation, when an object is sensed by the receiver 620, a capacitance is generated. The capacitance is then read by the receiver multiplexer 134 as described above. More specifically, assume that the transmitter 144d and the receiver 154d form a single cell. Accordingly, when an object is sensed, e.g. comes close to a cell formed by the receiver 154d and the receiver 154d, it forms a capacitance which is read when the system scans the cell that is composed of the transmitter 144d and the receiver 154d. It should be realized that the cells are continuously and iteratively scanned to determine when an object has contacted the sensor array. In the exemplary embodiment, the sensor array 18 is coupled to the gamma camera 18 or collimator 40 using an adhesive material 336. Sensor array 600 may act for example as the upper flexible pressure sensing plate 552 of PSD 550 flexible dividers 556 and lower pressure sensing plate 554 are not seen in this figure.

Figure 11:
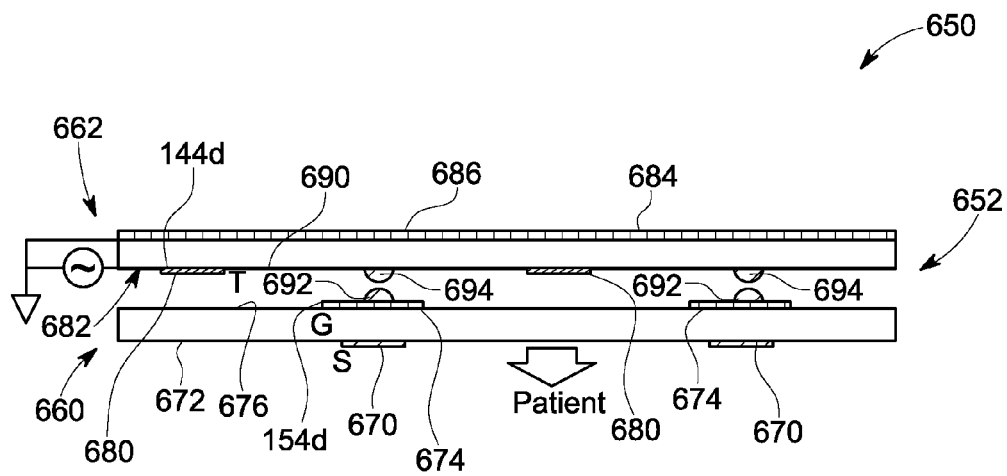
FIG. 11 is a side cross sectional view of still another exemplary proximity detection system (PDS) combined with a pressure safety device (PSD) formed in accordance with various embodiments.

FIG. 11 is side cross sectional view of a portion of another exemplary sensor array 650 that includes a proximity sensor system 652 that may be incorporated with the sensor array 650 or various other sensor arrays described herein. Specifically, FIG. 11 illustrates another embodiment of a proximity sensor and a flexible PSD formed in one device. For drawing clarity flexible dividers are not seen in this figure. In the exemplary embodiment, the sensor array 652 includes two PCBs 660 and 662. In the exemplary embodiment, a plurality of receivers 670 are disposed on a first side 672 of the PCB 660 and a plurality of ground plates 674 are disposed on a second side 676 of the PCB 660. The sensor array 650 further includes a plurality of transmitters 680 that are disposed on a first side 682 of the PCB 662 and an optional ground plate 674 that is disposed on a second side 676 of the PCB 660. The sensor array 650 further includes a plurality of electrical connection lines 690 that are disposed on the first side 682 of the PCB 662 to interconnect the transmitters 680. The sensor array 652 further includes a plurality of metallic pads 692. Optionally, each metallic pad 692 is coupled to a respective ground plate 674, and a plurality of metallic pads 694, located opposite to pad 692. Optionally each metallic pad 694 is coupled between a pair of transmitters 680. Pads 694 and 692 form a PSD such as PSD 550 seen in FIG. 4. For drawing clarity flexible dividers are not seen in this figure. In this embodiment layer 660 acts as flexible pressure sensing plate 552, while layer 662 acts as pressure sensing plate 554 and is closer to the patient.

In operation as a PSD, when an object contacts the plate 660, the flexible PCB 660 flexes or bends until at least one of the metallic pads 694 contacts a respective metallic pad 692. The metallic pad 694 contacting the metallic pad 692 causes an electrical circuit to be formed between the contacts signaling physical contact with an object. When acting as a PDS, sensor array 650 behaves as disclosed above.

Figure 12:
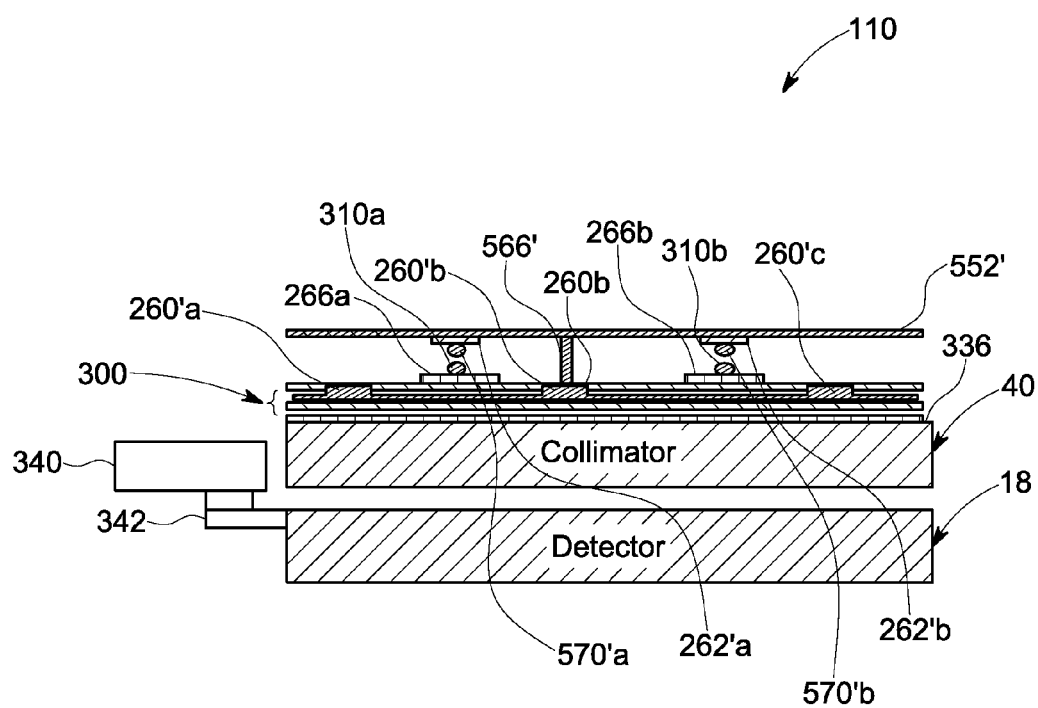
FIG. 12 is a side cross sectional view of a portion of a proximity detection system combined with a pressure safety device (PSD formed in accordance with various embodiments.

FIG. 12 is a side cross sectional view of a portion of the sensor array 110 shown in FIG. 1. In one embodiment, the sensor array 110 includes a plurality of transmitters 260' disposed on a printed circuit board (PCB) 300. In the exemplary embodiment, transmitters 260'a, 260'b, and 250'c are shown. PCB 300 may be flexible, or a rigid PCB if array 110 is flat. The PCB 300 is formed to include the various electrical connections that are utilized to connect the transmitters 260' to the transmitter multiplexer 132 as described above. Referring again to FIG. 12, the sensor array also includes a plurality of lower PSD contacts 310 (two such contacts: 310a and 310b are seen) that are electrically coupled to the PCB 300. Optionally, lower PSD contacts are places on, and in electrical contacts to ground electrode pads 266' (two such ground electrode pads 266'a and 266'b are seen in FIG. 12). The sensor array 110 further includes a flexible upper pressure sensing plate 552' which incorporates PSD contacts 570' and receivers 262' that is electrically separated from the PCB 300 using an insulating flexible dividers 556' (only one such separator is seen for drawing clarity). The flexible separator 320 may be fabricated for example from an insulating material, such as for example, a rubber material. The sensor array 110 further includes receivers 262' (two such receivers 262'a and 262'b are seen in this figure). As shown in FIG. 12, a metallic pad 570' is optionally coupled to each respective receiver 262'.

In operation as a PSD, when an object contacts the pressure plate 552', the flexible plate 552' flexes or bends such that at least one of the metallic contacts 570' contacts a respective metallic contact 310 on the PCB 300. In some embodiments, the direct electrical contact of the receiver to ground cased by pressure causes a strong decrease of the signal or elimination of the signal which may be interpreted as contact with the patient. In other embodiments, the PSD circuit optionally operates at a different frequency or at DC and is continuously monitored. For example, all the transmitters may be connected (via a coil or resistor) to some DC source. The DC current in the ground line (equivalent to line 362 in FIG. 9c) is zero as long as the PSD is not pressed and activated.

In operation as PDS, the AC signal is supplied to only one transmitters' column at a time and a signal is read from only one receivers' row at a time similarly to the way explained above. It should be realized that the cells are continuously and iteratively scanned to determine when an object has approached the sensor array. In the exemplary embodiment, the sensor array 110 is coupled to the gamma camera 18 or collimator 40, for example using an adhesive material 336.

The inputs and outputs to the sensor array, including the transmit multiplexer 132 and the receive multiplexer 134 may be housed within a single enclosure 340. In one embodiment the enclosure 340 may be coupled to a side of the gamma camera 18. Optionally, the enclosure 340 may be located remote from the gamma camera 18. In the exemplary embodiment, the enclosure 340 is coupled to the gamma camera 18 via a connector 342.

The above-described embodiments of a proximity detection system may provide a cost-effective and reliable means for examining a patient. In some embodiments, the imaging system includes a plurality of gamma cameras each having multiple degrees of freedom of movement, such that, during a scan, the gamma cameras may be automatically controlled, by the various sensor array described herein, to move the gamma cameras along a contour of the body of a patient to reduce the distance between the region of interest and the gamma camera sensitive face. An imaging system is also provided that may facilitate improving the resolution of the gamma cameras.

Exemplary embodiments of a proximity detection system are described above in detail. The automatic proximity detection system components illustrated are not limited to the specific embodiments described herein, but rather, components of each automatic proximity detection system may be utilized independently and separately from other components described herein. For example, the proximity detection system components described above may also be used in combination with other imaging systems.

A technical effect of the systems and methods described herein includes facilitating minimizing the distance between an organ of interest and an imaging system detector during an automatic imaging scan of a patient, and therefore facilitating reducing operator input to the scanning procedure and reducing the time necessary to perform a scan while improving the resolution of the imaging system.

The various embodiments and/or components, for example, the sensor arrays, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, the embodiments are by no means limiting and are exemplary embodiments. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A sensor array for a medical imaging system, said sensor array comprising:
a substrate configured to be mounted to a detector;

a proximity sensor array including a plurality of sensors, at least some of the sensors disposed on a first side of the substrate, the substrate being deformable to correspond to a sensing surface of the detector, wherein the plurality of sensors include a plurality of transmitters and a plurality of receivers arranged in rows and columns, the plurality of receivers in each row being coupled together in electrical series, wherein a first portion of the transmitters receive an input from a first input line, a second portion of the transmitters receive an input from a second input line, the first portion of transmitters being interleaved with the second portion of transmitters, wherein a single transmitter and a single receiver form a cell, the system configured to iteratively read each cell in sequence to identify when an object is proximate to the sensor array; and a conductive sensor array including a first plurality of metallic pads disposed on a second side of the substrate, the second side opposite the first side, the metallic pads configured to cooperate with a second plurality of metallic pads to close at least one circuit to indicate contact between the substrate and an object to be imaged.

2. The sensor array of claim 1, wherein the conductive sensor array comprises:
a printed circuit board that is separated from the substrate by a plurality of flexible dividers, the second plurality of metallic pads disposed on the printed circuit board, the plurality of flexible dividers defining separate sensing areas each sensing area comprising a corresponding one of the metallic pads of the first plurality of metallic pads and a corresponding one of the metallic pads of the second plurality of metallic pads, the corresponding metallic pads of the sensing area forming a circuit that outputs a signal indicating a location of the object when the object contacts the substrate to cause the corresponding metallic pads of the sensing area to contact each other.

3. The sensor array of claim 1, wherein the proximity sensor array includes a first column of transmitters and a second column of transmitters, the first column of transmitters being offset from the second column of transmitters.

4. The sensor array of claim 1, wherein the proximity sensor array includes a plurality of columns, at least one of the columns including a plurality of transmitters that are interleaved with a plurality of receivers.

5. The sensor array of claim 1, wherein the conductive sensor array comprises:
a printed circuit board;
a plurality of springs disposed between the substrate and the printed circuit board; and
at least one micro-switch configured to sense when the object contacts the substrate.

6. The sensor array of claim 1, further comprising:
a first non-conductive substrate configured to be mounted to the detector;
a second non-conductive substrate; and
a plurality of flexible separators springs disposed between the first and second non-conductive substrate, the flexible connectors defining a plurality of sensing areas, each sensing area comprising corresponding one of the metallic pads of the first plurality of metallic pads and a corresponding one of the metallic pads of the second plurality of metallic pads, the corresponding metallic pads of the sensing area forming a circuit that outputs a signal indicating a location of the object when the object contacts the substrate to cause the corresponding metallic pads of the sensing area to contact each other.

7. A method of fabricating a sensor array for an imaging system, said method comprising:
forming a plurality of sensors on a first side of a flexible substrate, the flexible substrate being deformable to correspond to a sensing surface of a detector, the sensors including a plurality of transmitters and a plurality of receivers arranged in rows and columns;
electrically coupling the plurality of receivers in each row in electrical series, wherein the plurality of sensors include a plurality of transmitters arranged columns;
disposing a plurality of metallic pads on a second side of the flexible substrate, the second side opposite the first side, the metallic pads configured to cooperate with a second plurality of metallic pads to close at least one circuit to indicate contact between the substrate and an object to be imaged;
coupling a first portion of the transmitters in a first column to a first input line, and
coupling a second portion of the transmitters in the first column to a second input line, the first portion of transmitters being interleaved with the second portion of transmitters.

8. The method of claim 7, wherein the sensor array includes a first column of transmitters and a second column of transmitters, the method further comprising offsetting the first column of transmitters from the second column of transmitters.

9. The method of claim 7, wherein the sensor array includes a plurality of columns, said method further comprising interleaving the plurality of transmitters in a first column with a plurality of receivers in the first column.

10. The method of claim 7, further comprising forming the sensor array to include:
a printed circuit board;
a plurality of springs disposed between the substrate and the printed circuit board; and
at least one micro-switch configured to sense when the object contacts the substrate.

11. The method of claim 7, further comprising forming the sensor array to include:
a first non-conductive substrate configured to be mounted to the detector;
a second non-conductive substrate; and
a plurality of flexible separators springs disposed between the first and second non-conductive substrate, the flexible connectors defining a plurality of sensing areas, each sensing area comprising a corresponding one of the metallic pads of the first plurality of metallic pads and a corresponding one of the metallic pads of the second plurality of metallic pads, the corresponding metallic pads of the sensing area forming a circuit that outputs a signal indicating a location of the object when the object contacts the substrate to cause the corresponding metallic pads of the sensing area to contact each other.

12. A medical imaging system comprising:
a gantry;
at least one gamma camera coupled to the gantry;
a proximity sensor array coupled to the gamma camera, the proximity sensor array including:
a flexible substrate configured to be mounted to the gamma camera; and
a plurality of sensors disposed on a first side of the flexible substrate, the flexible substrate being deformable to contact a sensing surface of the gamma camera, wherein the sensors include a plurality of transmitters and a plurality of receivers arranged in rows and columns, the plurality of receivers in each row being coupled together in electrical series; and a conductive sensor array including a first plurality of metallic pads disposed on a second side of the substrate, the second side opposite the first side, the metallic pads configured to cooperate with a second plurality of metallic pads to close at least one circuit to indicate contact between the substrate and an object to be imaged.

13. The imaging system of claim 12, wherein a first portion of the transmitters receive an input from a first input line, a second portion of the transmitters receive an input from a second input line, the first portion of transmitters being interleaved with the second portion of transmitters.

14. The imaging system of claim 12, wherein a single transmitter and a single receiver form a cell, the system configured to iteratively read each cell in sequence to identify when an object is contacting the sensor array.

15. The imaging system of claim 12, wherein the conductive sensor array comprises:
a flexible printed circuit board that is separated from the flexible substrate by a plurality of flexible dividers, the second plurality of metallic pads disposed on the printed circuit board, the plurality of flexible dividers defining separate sensing areas, each sensing area comprising a corresponding one of the metallic pads of the first plurality of metallic pads and a corresponding one of the metallic pads of the second plurality of metallic pads, the corresponding metallic pads of the sensing area forming a circuit that outputs a signal indicating a location of the object when the object contacts the substrate to cause the corresponding metallic pads of the sensing area to contact each other.

16. The imaging system of claim 12, wherein the proximity sensor array includes a first column of transmitters and a second column of transmitters, the first column of transmitters being offset from the second column of transmitters.

17. The imaging system of claim 12, wherein the proximity sensor array includes a plurality of columns, at least one of the columns including a plurality of transmitters that are interleaved with a plurality of receivers.

18. The imaging system of claim 12, wherein the conductive sensor array comprises:
a printed circuit board;
a plurality of springs disposed between the flexible substrate and the printed circuit board; and
at least one micro-switch configured to sense when the object contacts the substrate.

19. The imaging system of claim 12, wherein the conductive sensor array further comprises:
a first non-conductive substrate configured to be mounted to the detector;
a second non-conductive substrate; and
a plurality of flexible separators springs disposed between the first and second non-conductive substrate, the flexible connectors defining a plurality of sensing areas, each sensing area comprising a corresponding one of the metallic pads of the first plurality of metallic pads and a corresponding one of the metallic pads of the second plurality of metallic pads, the corresponding metallic pads of the sensing area forming a circuit that outputs a signal indicating a location of the object when the object contacts the substrate to cause the corresponding metallic pads of the sensing area to contact each other.

20. The sensor array of claim 1, wherein at least some of the transmitters are disposed on the second side of the substrate, each of the first plurality of metallic pads being disposed between a pair of the at least some of the transmitters.

* * * * *